(12) United States Patent
Niu et al.

(10) Patent No.: US 8,687,192 B2
(45) Date of Patent: Apr. 1, 2014

(54) THROUGH SILICON IMAGING AND PROBING

(75) Inventors: Baohua Niu, Portland, OR (US);
Patrick M. Pardy, Hillsboro, OR (US);
David L. Budka, Langhorne, PA (US);
Mitchell L. Sacks, Aloha, OR (US)

(73) Assignee: Intel Corporation, Santa Clara, CA (US)

( * ) Notice: Subject to any disclaimer, the term of this patent is extended or adjusted under 35 U.S.C. 154(b) by 328 days.

(21) Appl. No.: 13/074,877

(22) Filed: Mar. 29, 2011

(65) Prior Publication Data
US 2012/0249859 A1    Oct. 4, 2012

(51) Int. Cl.
*G01J 4/00*    (2006.01)
(52) U.S. Cl.
USPC ........................................................... 356/369

(58) Field of Classification Search
USPC .................................................. 356/364–370
See application file for complete search history.

(56) References Cited

U.S. PATENT DOCUMENTS

| | | | | |
|---|---|---|---|---|
| 5,788,632 A | * | 8/1998 | Pezzaniti et al. | 600/316 |
| 2010/0149519 A1 | * | 6/2010 | Toofan | 356/51 |

* cited by examiner

*Primary Examiner* — Tara S Pajoohi Gomez
(74) *Attorney, Agent, or Firm* — Blakely, Sokoloff, Taylor & Zafman LLP

(57) ABSTRACT

Through silicon imaging and probing. A light source provides unpolarized light to be projected on a device under test (DUT). Light reflected from the DUT may be captured by a camera or other image capture device. A pellicle is utilized to reflect light from the light source toward the DUT. The pellicle also passes light reflected by the DUT to the camera. One or more linear polarizers or half wave plates may be used to provide the desired light polarization. The ability to provide the desired polarization provides an improved image that can be captured by the camera.

18 Claims, 10 Drawing Sheets

THROUGH SILICON IMAGING AND PROBING

TECHNICAL FIELD

Embodiments of the invention relate to techniques for imaging and probing of integrated devices. More particularly, embodiments of the invention relate to techniques for improved optical probing sensitivity and imaging resolution of integrated devices.

BACKGROUND

When an integrated device product (e.g., packaged silicon/die) is loaded into a tester for platform environment docked to an optical backside tool (e.g., Infrared Emission (IREM) device, Time Resolved Emission (TRE) device, Laser Assisted Device Alteration (LADA) device, Laser Voltage Probing (LVP) device, Laser Stimulated Emission Detection (LSTED) device) and imaged through the backside to perform optical probing, the orientation of the product may influence the ability to align the product and pinpoint devices for debugging. The alignment difficulties may be the result of asymmetric circuit layouts.

The asymmetric circuit layout can cause illuminated light to be preferably absorbed and partially reflected while in one orientation, and fully reflected while in another orientation, degrading both the contrast and resolution of the resulting image if not properly corrected. If the product is oriented 90 from the optimal position, the imaging of the integrated device structures may be obscured creating a localization and data acquisition gap in performance of the optical tool.

BRIEF DESCRIPTION OF THE DRAWINGS

Embodiments of the invention are illustrated by way of example, and not by way of limitation, in the figures of the accompanying drawings in which like reference numerals refer to similar elements.

DETAILED DESCRIPTION

Figure 1:
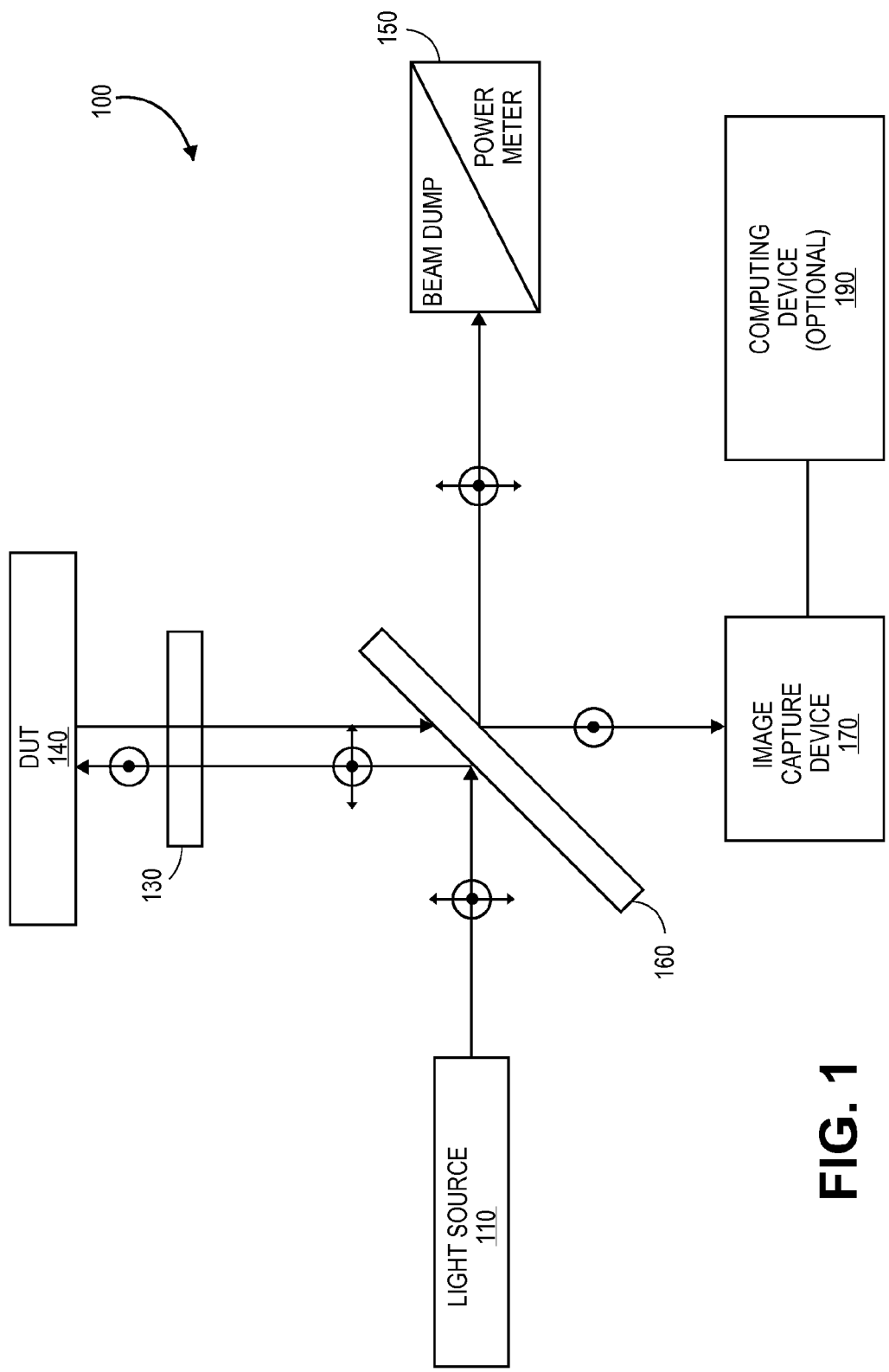
FIG. 1 is a block diagram of one embodiment of a mechanism for optical probing and/or imaging of a device under test (DUT).

In the following description, numerous specific details are set forth. However, embodiments of the invention may be practiced without these specific details. In other instances, well-known circuits, structures and techniques have not been shown in detail in order not to obscure the understanding of this description.

Described herein are imaging and probing techniques that may provide a correction for the image degradation by taking advantage of the interaction of linear polarized light with the asymmetric integrated circuit layout, and taking advantage of the asymmetric layout that causes the absorption and partial reflection, and emission of the linear polarized light depending on circuit layout orientation. These techniques may also correct the reflected or emitted light to yield better imaging contrast and resolution. These techniques may also reduce data collection time while optically probing circuits of interest due to enhanced returned light which has emission or modulated data contained within.

Various embodiments of mechanisms that may provide improved optical probing and imaging are described below. In one embodiment, three optical elements may be utilized and configured for illumination and may be adjustable to optimize both the transmitted and reflected light paths to improve imaging and localization of devices. As one example, these three optical components may include a linear polarizer, an optical half wave plate and an optical pellicle.

In one embodiment, the pellicle may be at an angle that reflects linear polarized light towards the optical half wave plate. The optical half wave plate may be adjusted to impose the correct polarization orientation of light, through silicon, onto the asymmetrical structure layout attributes of the device on the die. This overall optimization of light, reflection of the pellicle and optimized rotation of the half wave plate, work together to provide improved light intensity, with the correct polarization orientation of the light, to reach the silicon such that the partial absorption and reflection of the light is utilized and the reflected light contains crisp and accurate information for both imaging and data collection.

Prior to utilization of the techniques described herein there existed no solution for backside optical debug and/or imaging that did not suffer from the imaging gap due to the asymmetric properties and its interactions with polarized light discussed above. The asymmetric properties of the integrated circuits cause the reflection and transmission of the incident light intensity dependent on the polarization direction. The device's layout properties and materials may absorb the electric field, thus lowering the reflected light's intensity. The techniques described herein function to recover the light intensity, delivering peak light for imaging and emission data, as well as waveform capture.

Described herein are various techniques to optimize the incident light impingent onto a pellicle, ensuring more of the light is aligned/optimized to the reflected plane of the pellicle. This provides that the light leaving the pellicle, toward the silicon, is optimized for peak intensity at the correct polarized angle. This optimized peak intensity is then rotated by the half wave plate to counter the asymmetric absorption properties of the silicon layout as it is transmitted onto the die. The returned/reflected light from the silicon is then transmitted through the pellicle for imaging.

FIG. 1 is a block diagram of one embodiment of a mechanism for optical probing and/or imaging of a device under test (DUT). System 100 includes the elements illustrated in FIG. 1 as well as other elements not illustrated in FIG. 1. Light source 110 provides unpolarized light to be used to illuminate DUT 140, which can be, for example, an integrated circuit die, or other similar device.

The unpolarized light is generally reflected by pellicle 160 toward DUT 140. Pellicle 160 may provide a partial polarization of the light from light source 110. Some of the unpolarized light my pass through pellicle 160 and may be absorbed by beam dump 150. Beam dump 150 may be replaced by a power meter that may allow a light measurement that can be used to determine the strength of the light directed at DUT 140. The portion of the partially polarized light that is reflected by pellicle 160 is directed to DUT 140 through optical half wave plate 130. In one embodiment, optical half wave plate 130 is rotatable.

Light reflected from DUT 140 back to pellicle 160 also passes through optical half wave plate 130 in the reverse direction. The light reflected back from DUT 140 through optical half wave plate 130 also passes through pellicle 160 to image capture device 170. The light passing through pellicle 160 may be partially polarized by pellicle 160.

Image capture device 170 may be utilized to capture images of DUT 140. Image capture device 170 may be, for example, a liquid nitrogen (LN2) or thermoelectrically cooled (TEC) InGaAs Focal Plan Array (FPA) camera with pixel counts of 32×256, 640×512, 640×640, 1024×1024, and 1280×1024. Other camera types and resolutions may also be used.

In one embodiment, image capture device 170 may provide feedback, to or through system 100, that may be utilized to rotate optical half wave plate 130 to provide improved imaging of DUT 140. The polarization of the light projected on DUT 140 influences the quality of the image captured. By using an output image from image capture device 170 as feedback in rotating optical half wave plate 130, an improved image may be acquired.

Image capture device 170 may be coupled with computing device 190 which may provide image analysis of the images captured by image capture device 170. In one embodiment, computing device 190 may function to align two or more images recorded by image capture device 170 using different linear polarization directions relative to the features of interest on DUT 140. Computing device 190 may operate to provide a pixel-by-pixel summation or subtraction of the two or more images to generate a difference image that may have improved image contrast and/or resolution compared to the original images.

With increasingly small geometries in semiconductor devices, previous techniques for optical probing and imaging were often insufficient. In one embodiment two or more images (e.g., Infrared (IR) or Near IR (NIR)) may be taken and analyzed to provide an improved overall image.

As discussed above, semiconductor devices on the DUT may be asymmetric with regard to their x-axis and y-axis orientation and dimension. Linear polarized NIR and IR light will reflect and transmit through the semiconductor differently depending on the orientation of the features of interest on the DUT due to preferred absorption of the NIR and IR polarized light along certain orientation.

The different image contrast and resolution afforded with the linear polarized NIR and/or IR light provides the ability to obtain two or more images of the features of interest with different polarized NIR and IR light. The differences among the images obtained with different polarizations may be pixel by pixel enhanced, which may enable better image contrast and better resolution.

Figure 2:
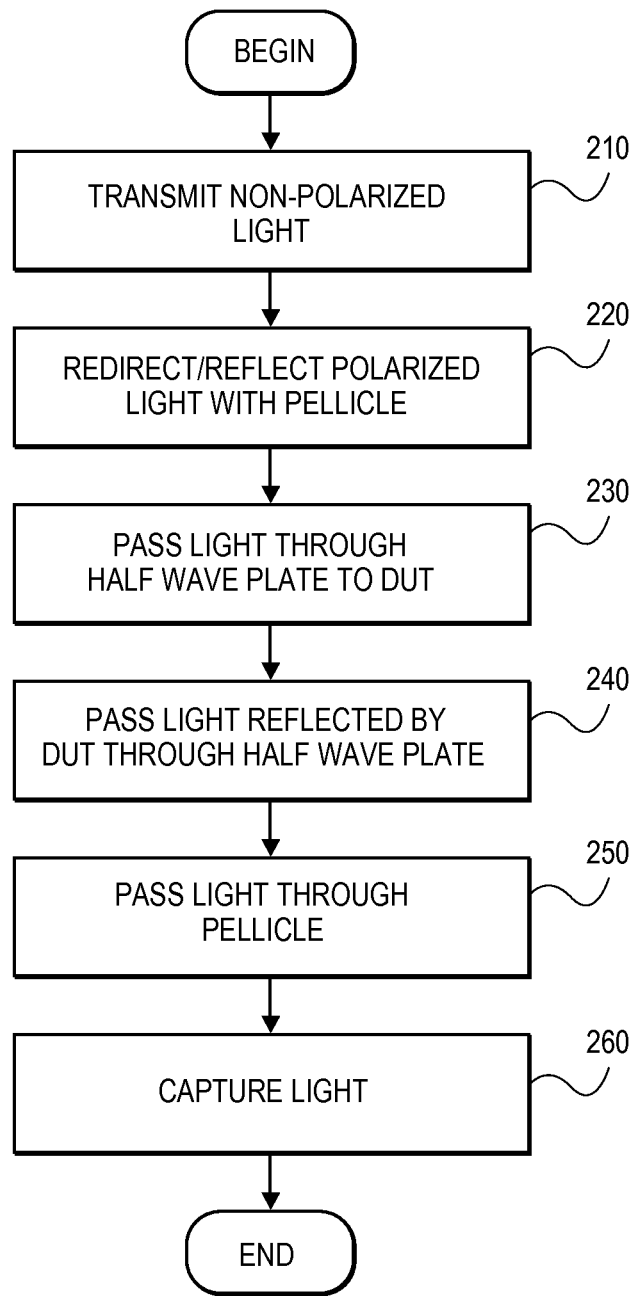
FIG. 2 is a flow diagram of a technique for optical probing and/or imaging of a DUT using the system of FIG. 1.

FIG. 2 is a flow diagram of a technique for optical probing and/or imaging of a DUT. The technique described with respect to FIG. 2 may be accomplished, for example, using the system of FIG. 1.

Non-polarized light is projected from a light source, 210. The light source may be projected by any source capable of providing light for optical probing and/or semiconductor device imaging. In one embodiment, the unpolarized light may be reflected/redirected by a pellicle, 220, to partially polarize the light and redirect the partially polarized light toward a DUT. As described above, some light my pass through the pellicle and be absorbed by a beam dump or other component.

The light that is reflected/redirected by the pellicle toward the DUT is passed through an optical half wave plate, 230. In one embodiment, the optical half wave plate may be rotated to provide the desired polarization of the light on the DUT. The light that passes through the optical half wave plate is reflected by the DUT back through the optical half wave plate in the opposite direction, 240.

After passing through the optical half wave plate, the light passes through the pellicle 250. The light that passes through the pellicle may be captured, 260, by any appropriate image capture device. Examples of image capture devices that may be used are listed above.

Figure 3:
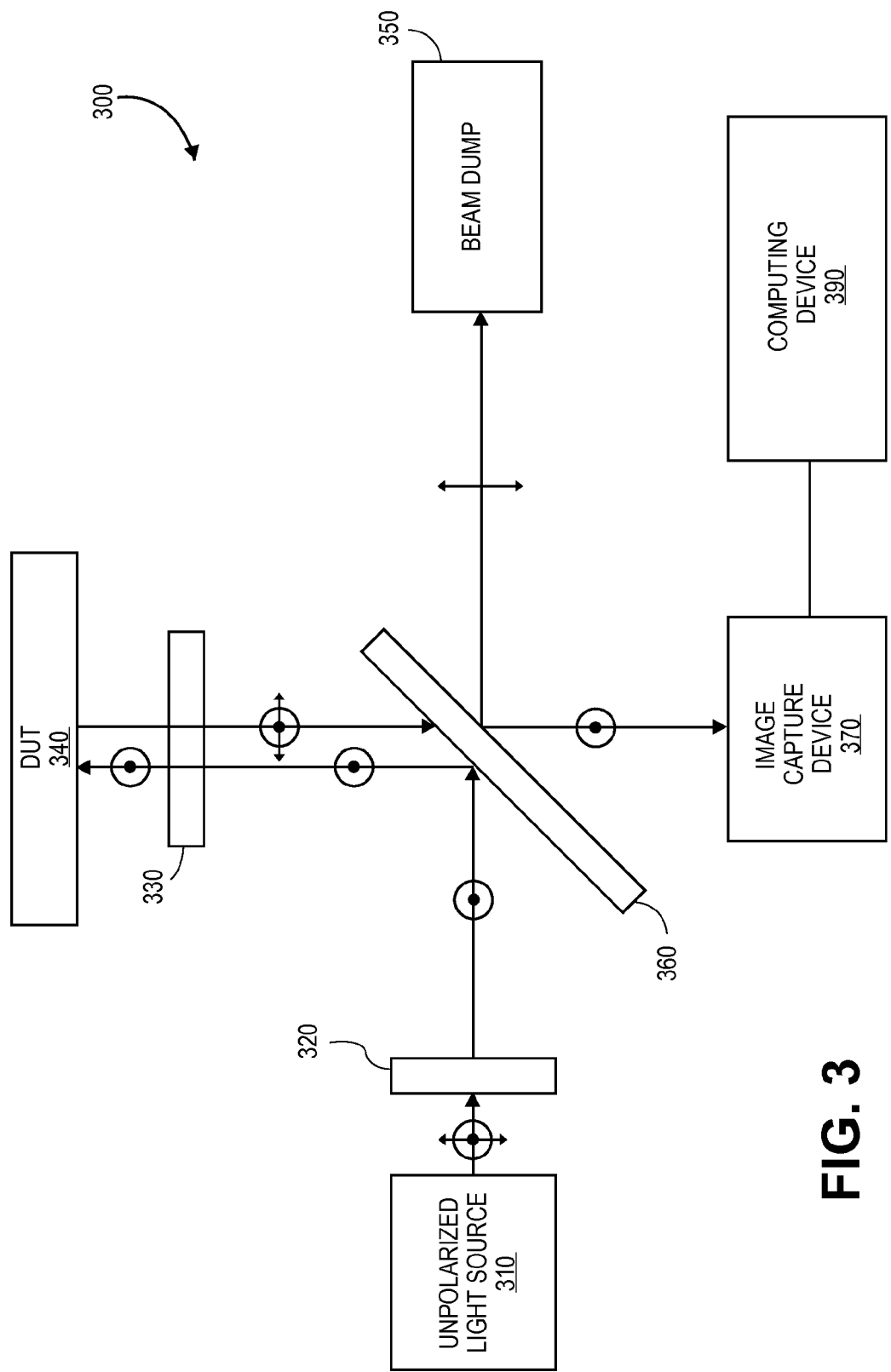
FIG. 3 is a block diagram of one embodiment of a mechanism for optical probing and/or imaging of a DUT.

FIG. 3 is a block diagram of one embodiment of a mechanism for optical probing and/or imaging of a DUT. The device illustrated in FIG. 3 may provide optical probing and/or image capture of the DUT.

System 300 includes the elements illustrated in FIG. 3 as well as other elements not illustrated in FIG. 3. Light source 310 provides unpolarized light to be used to illuminate DUT 340, which can be, for example, an integrated circuit die, or other similar device. Light projected by light source 310 passes through optical linear polarizer 320 to provide polarized light.

The polarized light is generally reflected by pellicle 360 toward DUT 340. Some of the polarized light my pass through pellicle 360 and may be absorbed by beam dump 350. The portion of the polarized light that is reflected by pellicle 360 is directed to DUT 340 through optical half wave plate 330. In one embodiment, optical half wave plate 330 is rotatable.

Light reflected from DUT 340 back to pellicle 360 also passes through optical half wave plate 330 in the reverse direction. The light reflected back from DUT 340 through optical half wave plate 330 also passes through pellicle 360 to camera 370. Image capture device 370 may be utilized to capture images of DUT 340.

In one embodiment, image capture device 370 may provide feedback, to or through system 300, that may be utilized to rotate optical half wave plate 330 to provide improved imaging of DUT 340. As discussed above, the polarization of the light projected on DUT 340 influences the quality of the image captured. By using an output image from image capture device 370 as feedback in rotating optical half wave plate 330, an improved image may be acquired.

Image capture device 370 may be coupled with computing device 390 which may provide image analysis of the images captured by image capture device 370. In one embodiment, computing device 390 may function to align two or more images recorded by image capture device 370 using different linear polarization directions relative to the features of interest on DUT 340. Computing device 390 may operate to provide a pixel-by-pixel summation or subtraction of the two or more images to generate a difference image that may have improved image contrast and/or resolution compared to the original images.

Figure 4:
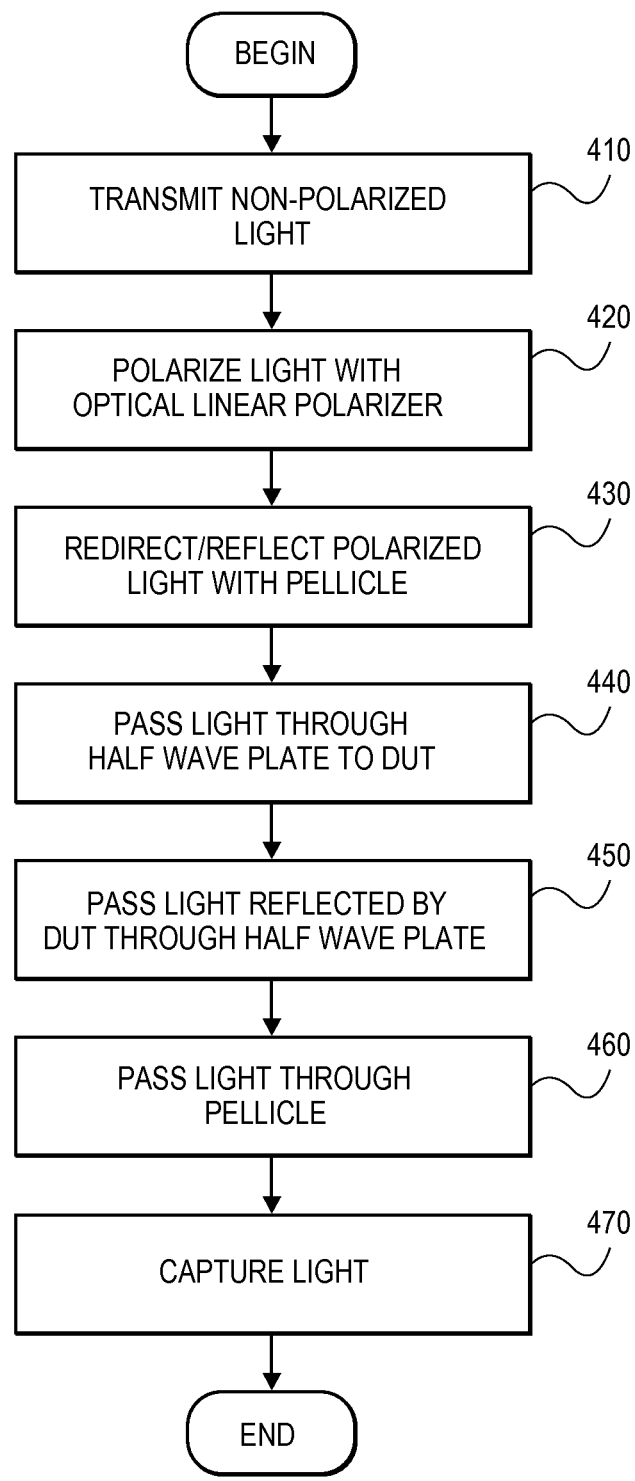
FIG. 4 is a flow diagram of a technique for optical probing and/or imaging of a DUT using the system of FIG. 3.

FIG. 4 is a flow diagram of a technique for optical probing and/or imaging of a DUT. The technique described with respect to FIG. 4 may be accomplished, for example, using the system of FIG. 3.

Non-polarized light is projected from a light source, 410. The light source may be projected by any source capable of providing light for optical probing and/or semiconductor device imaging. The non-polarized light is polarized, 420, by passing through an optical linear polarizer. In one embodiment, the polarized light may be reflected/redirected by a pellicle, 430, to redirect the light toward a DUT. As described above, some light my pass through the pellicle and be absorbed by a beam dump or other component.

The light that is reflected/redirected by the pellicle toward the DUT is passed through an optical half wave plate, 440. In one embodiment, the optical half wave plate may be rotated to provide the desired polarity on the DUT. The light that passes through the optical half wave plate is reflected by the DUT back through the optical half wave plate in the opposite direction, 450.

After passing through the optical half wave plate, the light passes through the pellicle 460. The light that passes through the pellicle may be captured, 470, by any appropriate image capture device. Examples of image capture devices that may be used are listed above.

Figure 5:
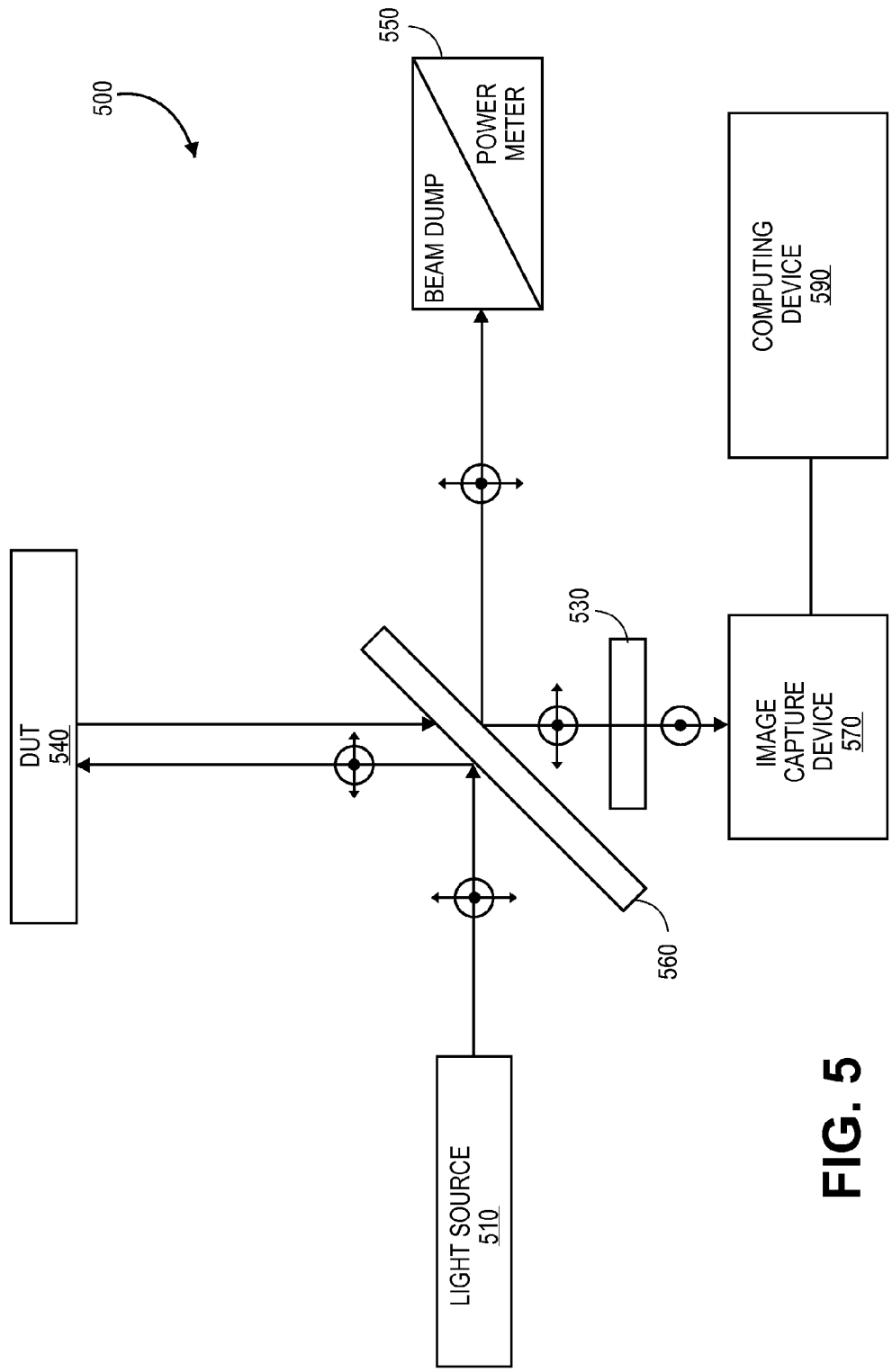
FIG. 5 is a block diagram of one embodiment of a mechanism for optical probing and/or imaging of a DUT.

FIG. 5 is a block diagram of one embodiment of a mechanism for optical probing and/or imaging of a DUT. The device illustrated in FIG. 5 may provide optical probing and/or image capture of the DUT.

System 500 includes the elements illustrated in FIG. 5 as well as other elements not illustrated in FIG. 5. Light source 510 provides unpolarized light to be used to illuminate DUT 540, which can be, for example, an integrated circuit die, or other similar device. The unpolarized light is generally reflected and partially polarized by pellicle 560 toward DUT 540. Some of the unpolarized light my pass through pellicle 560 and may be absorbed by beam dump and/or power meter 550. The portion of the polarized light that is reflected by pellicle 560 is directed to DUT 540.

Light reflected from DUT 540 back to pellicle 560 also passes through pellicle 560 to image capture device 570 through half wave plate 530. In one embodiment, half wave plate 530 is rotatable to provide the desired polarization to image capture device 570. Image capture device 570 may be utilized to capture images of DUT 540.

In one embodiment, image capture device 570 may provide feedback, to or through system 500, that may be utilized to rotate optical half wave plate 530 to provide improved imaging of DUT 540. As discussed above, the polarization of the light projected on DUT 540 influences the quality of the image captured. By using an output image from image capture device 570 as feedback in rotating optical half wave plate 530, an improved image may be acquired.

Image capture device 570 may be coupled with computing device 590 which may provide image analysis of the images captured by image capture device 570. In one embodiment, computing device 590 may function to align two or more images recorded by image capture device 570 using different linear polarization directions relative to the features of interest on DUT 540. Computing device 590 may operate to provide a pixel-by-pixel summation or subtraction of the two or more images to generate a difference image that may have improved image contrast and/or resolution compared to the original images.

Figure 6:
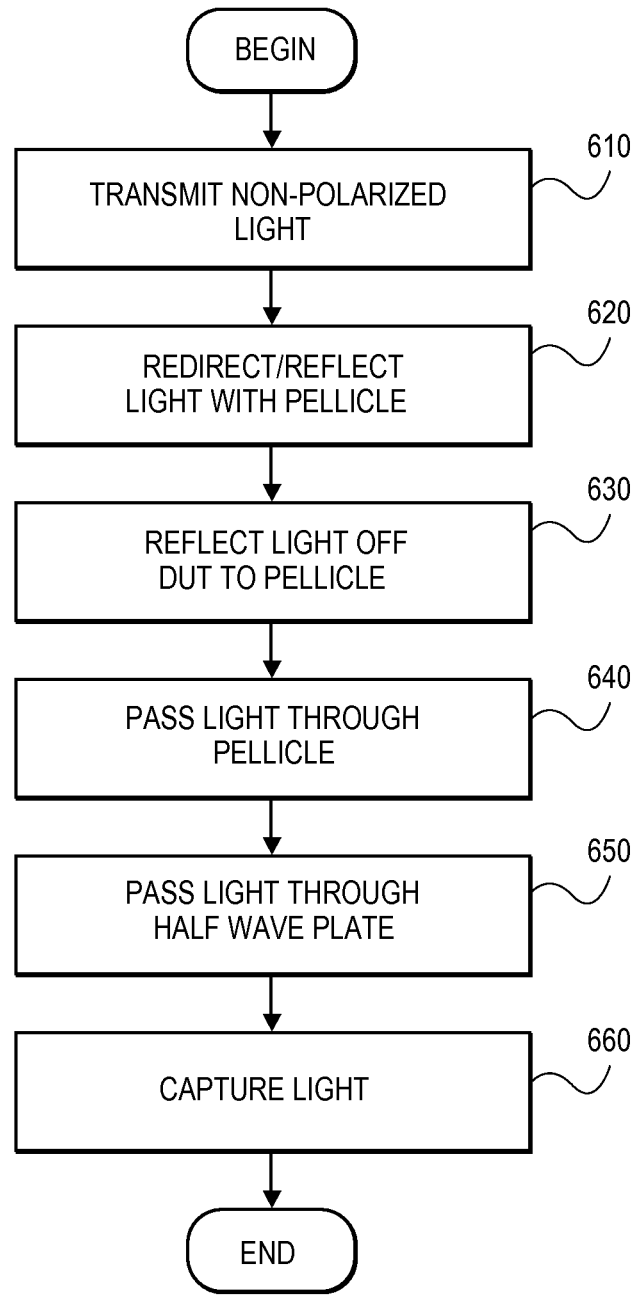
FIG. 6 is a flow diagram of a technique for optical probing and/or imaging of a DUT using the system of FIG. 5.

FIG. 6 is a flow diagram of a technique for optical probing and/or imaging of a DUT. The technique described with respect to FIG. 6 may be accomplished, for example, using the system of FIG. 5.

Non-polarized light is projected from a light source, 610. The light source may be projected by any source capable of providing light for optical probing and/or semiconductor device imaging. In one embodiment, the nonpolarized light may be reflected/redirected by a pellicle, 620, to redirect the light toward a DUT. As described above, some light my pass through the pellicle and be absorbed by a beam dump or other component.

The light that is reflected/redirected by the pellicle toward the DUT is reflected by the DUT back to the pellicle, 630. After passing through the pellicle, 640, the light is passed through an optical half wave plate, 650. The light that passes through the half wave plate may be captured, 660, by any appropriate image capture device. Examples of image capture devices that may be used are listed above.

Figure 7:
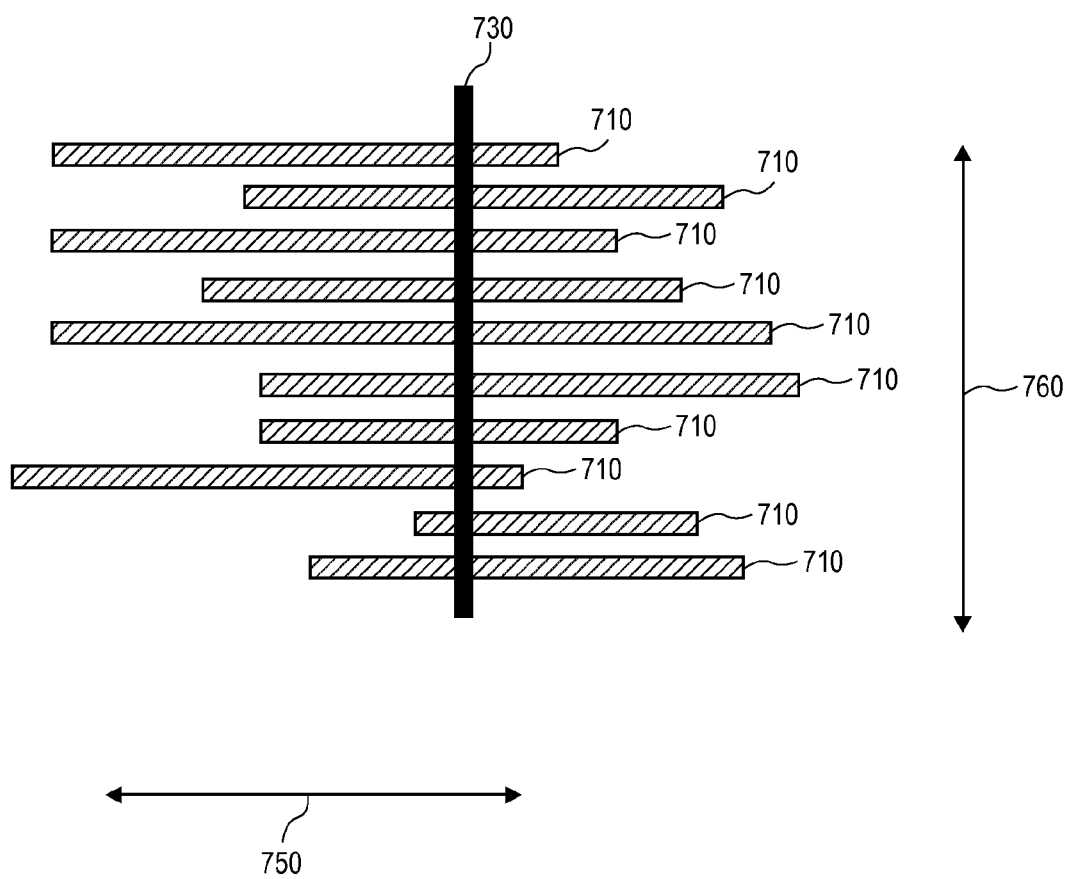
FIG. 7 is a diagram of a simplified circuit feature array that may represent structures on a DUT.

FIG. 7 is a diagram of a line array that may represent structures on a DUT. For smaller manufacturing processes (e.g., less than 45 nm), device structures may include parallel lines as indicated by lines 710. These parallel line arrays my function as a polarizer for light directed at the DUT causing the reflected light to be polarized.

Light having a horizontal polarization (i.e., parallel to lines 710), as indicated by polarization 750, may result in an image with poor resolution because of optical glare caused by lines 710. This glare can be compared to light reflected by wet pavement after rain. Polarization provided by the various components discussed above can compensate in a manner similar to a person wearing sunglasses.

Light having a vertical polarization (i.e., perpendicular to lines 710), as indicated by polarization 760, may result in an image with improved resolution as compared to the horizontal polarization. Thus, control of the light polarization with the mechanisms discussed above can provide the ability to obtain an image with improved resolution. Cut line 730 is a line along which the features of FIG. 7 may be analyzed graphically as described below.

Figure 8A:
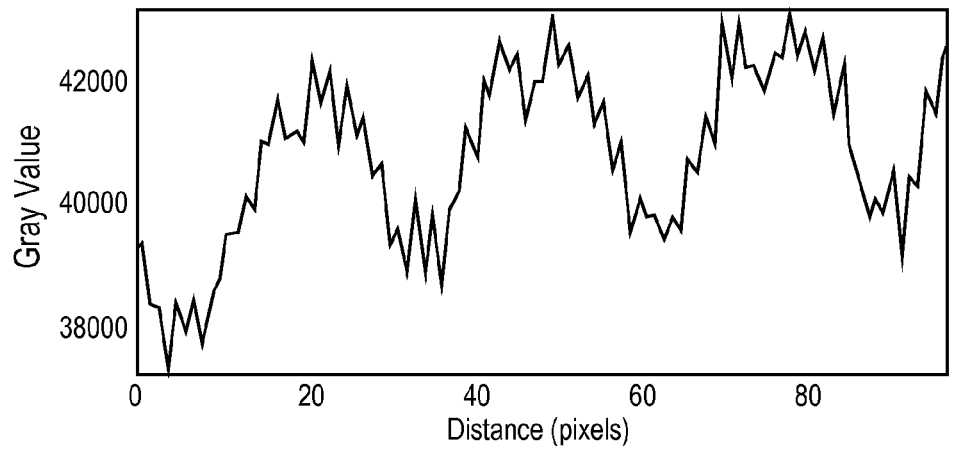
FIGS. 8a-8c illustrate example line scan graphs for images captured with parallel polarized light (FIG. 8a), perpendicularly polarized light (FIG. 8b) and a difference between the two (FIG. 8c).
Figure 8B:
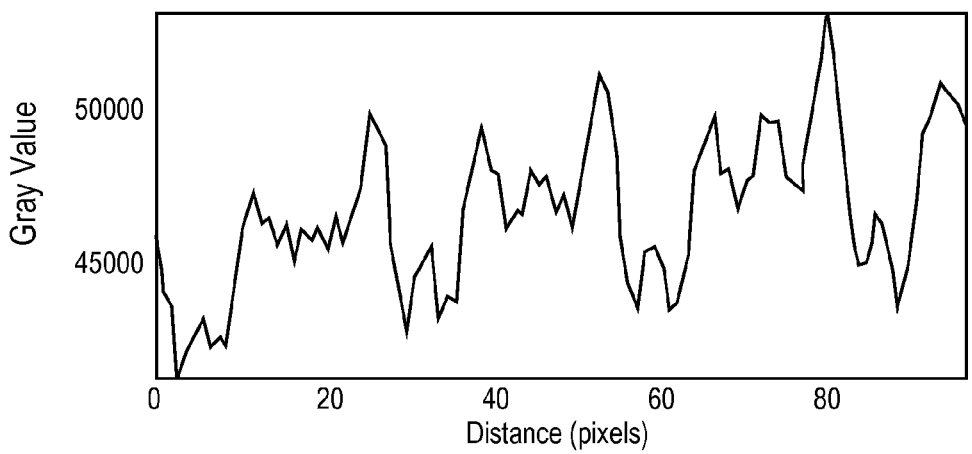
Figure 8C:
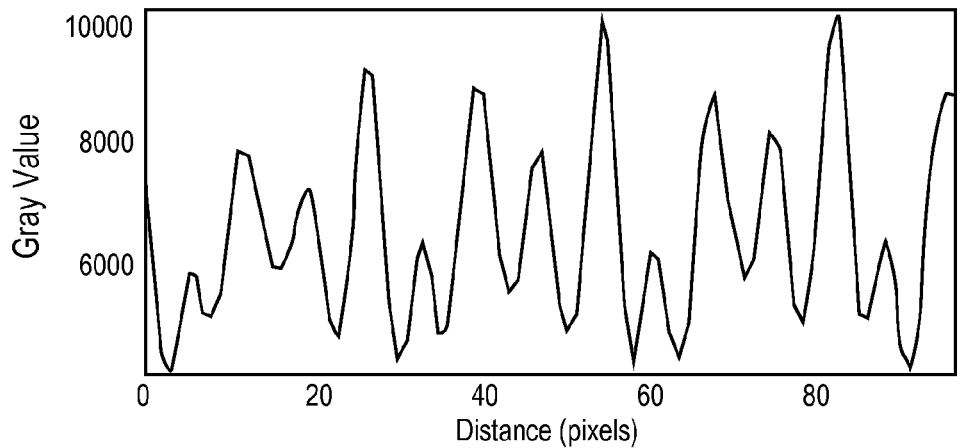

In one embodiment, images with both vertical polarization and horizontal polarization may be utilized to achieve an image with resolution better than either of the base images. FIGS. 8a-8c illustrate example line scan graphs for images captured with parallel polarized light (FIG. 8a), perpendicularly polarized light (FIG. 8b) and a difference between the two (FIG. 8c).

Figure 9:
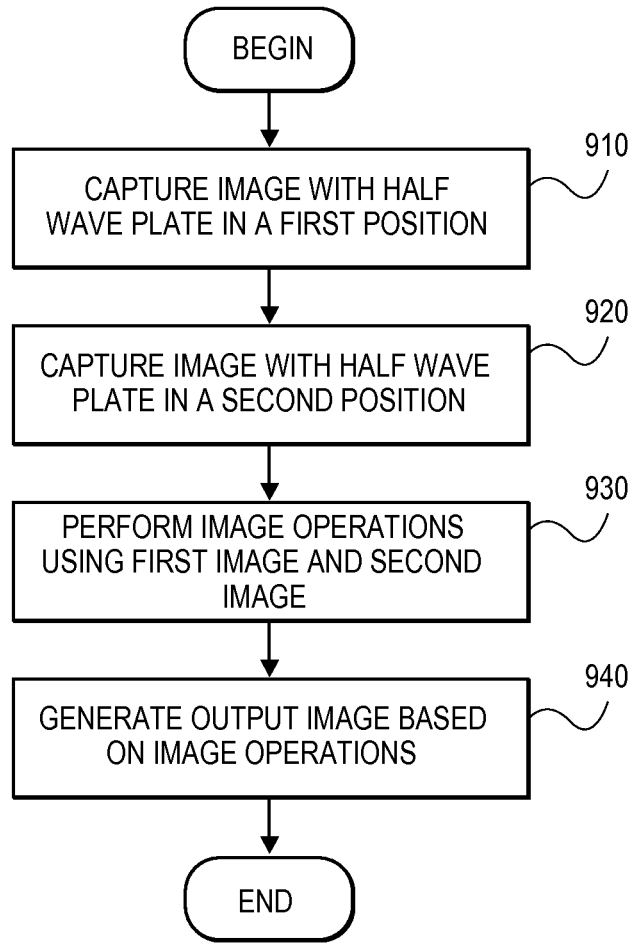
FIG. 9 is a flow diagram of a technique for using multiple images obtained my optical probing and/or imaging to produce an improved image.

FIG. 9 is a flow diagram of a technique for using multiple images obtained my optical probing and/or imaging to produce an improved image. In one embodiment, the technique of FIG. 9 is utilized in conjunction with, for example, the systems described above.

A first image is captured with the optical half wave plate in a first position, 910. The process used to capture the first image may be, for example, the image capture devices discussed above.

The optical half wave plate may then be rotated. In one embodiment, the system providing the optical probing and/or image capture may provide a real time image corresponding to the image received by the image capture device. This feedback may be utilized by a user of the system to rotate the optical half wave plate to provide the desired contrast and image quality.

A second image is captured with the optical half wave plate in a second position, 920. In one embodiment, position refers to rotation of the optical half wave plate. In alternate embodiments, other position changes may be made to the optical half wave plate. The process used to capture the second image may be, for example, the image capture devices discussed above.

Image operations are performed using the first image and the second image, 930. The image operations may include, for example, alignment and pixel-by-pixel subtraction of pixel values of one image from the other image. Alternatively, image operations may include, for example, alignment and pixel-by-pixel addition of pixel values of one image from the other image. Other image operations may also be performed.

The result of the image operations may be used to generate an output image, 940. The output image may be displayed to a user of the system, or may be stored on a data storage device for later retrieval, or transmitted to a remote location, etc. The output image generally provides better contrast and/or resolution than either the first image or the second image alone.

Figure 10:
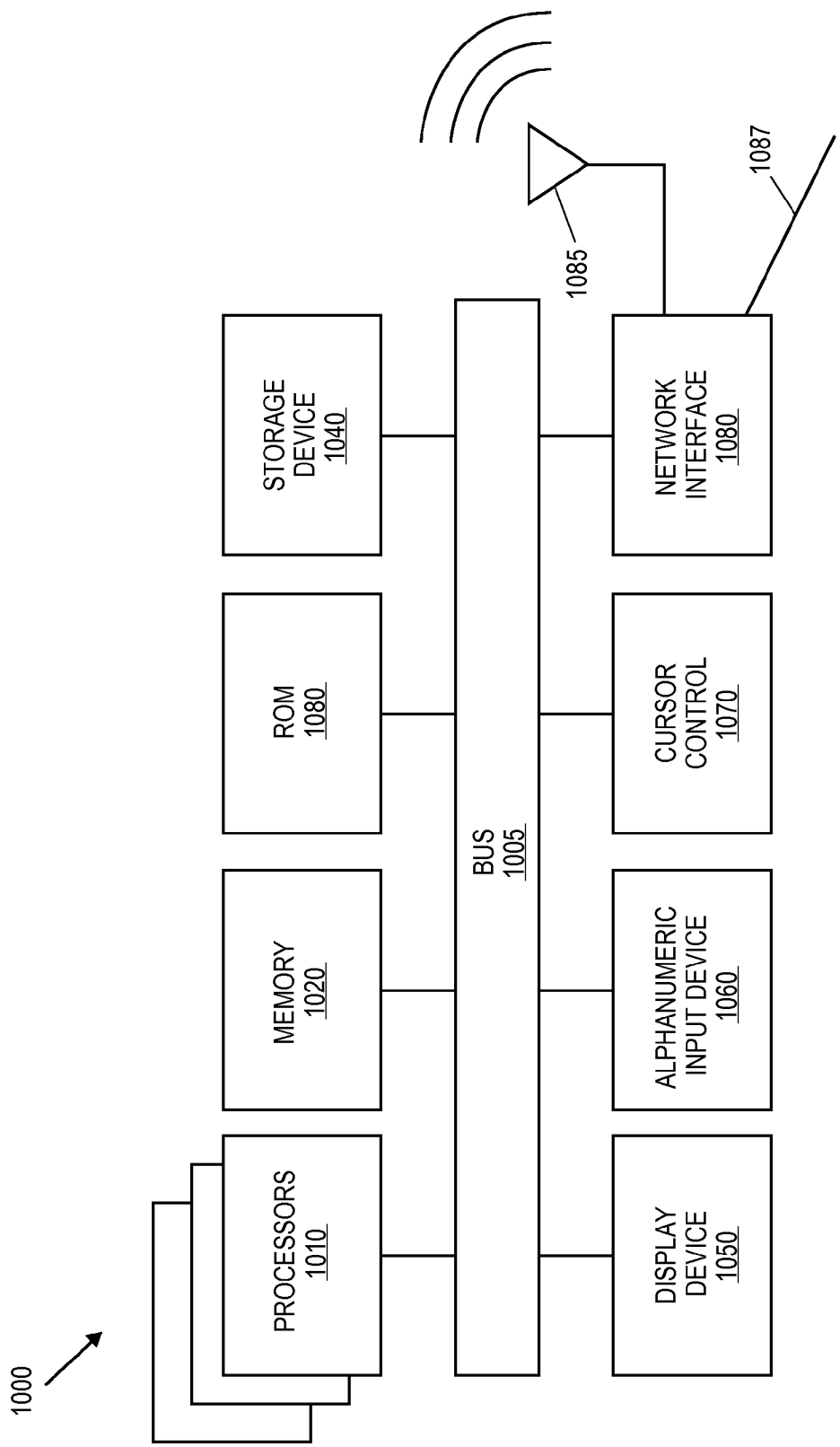
FIG. 10 is a block diagram of one embodiment of an electronic system.

FIG. 10 is a block diagram of one embodiment of an electronic system. The electronic system illustrated in FIG. 10 is intended to represent a range of electronic systems (either wired or wireless) including, for example, desktop computer systems, laptop computer systems, cellular telephones, personal digital assistants (PDAs) including cellular-enabled PDAs, set top boxes. Alternative electronic systems may include more, fewer and/or different components. The electronic system of FIG. 10 may be utilized to control the systems of FIGS. 1 and 2, and/or to perform some or all of the processes outlined in FIGS. 3 and 4.

Electronic system 1000 includes bus 1005 or other communication device to communicate information, and processor 1010 coupled to bus 1005 that may process information. While electronic system 1000 is illustrated with a single processor, electronic system 1000 may include multiple processors and/or co-processors. Electronic system 1000 further may include random access memory (RAM) or other dynamic storage device 1020 (referred to as main memory), coupled to bus 1005 and may store information and instructions that may be executed by processor 1010. Main memory 1020 may also be used to store temporary variables or other intermediate information during execution of instructions by processor 1010.

Electronic system 1000 may also include read only memory (ROM) and/or other static storage device 1030 coupled to bus 1005 that may store static information and instructions for processor 1010. Data storage device 1040 may be coupled to bus 1005 to store information and instructions. Data storage device 1040 such as a magnetic disk or optical disc and corresponding drive may be coupled to electronic system 1000.

Electronic system 1000 may also be coupled via bus 1005 to display device 1050, such as a cathode ray tube (CRT) or liquid crystal display (LCD), to display information to a user. Alphanumeric input device 1060, including alphanumeric and other keys, may be coupled to bus 1005 to communicate information and command selections to processor 1010. Another type of user input device is cursor control 1070, such as a mouse, a trackball, or cursor direction keys to communicate direction information and command selections to processor 1010 and to control cursor movement on display 1050.

Electronic system 1000 further may include network interface(s) 1080 to provide access to a network, such as a local area network. Network interface(s) 1080 may include, for example, a wireless network interface having antenna 1085, which may represent one or more antenna(e). Network interface(s) 1080 may also include, for example, a wired network interface to communicate with remote devices via network cable 1087, which may be, for example, an Ethernet cable, a coaxial cable, a fiber optic cable, a serial cable, or a parallel cable.

In one embodiment, network interface(s) 1080 may provide access to a local area network, for example, by conforming to IEEE 802.11b and/or IEEE 802.11g standards, and/or the wireless network interface may provide access to a personal area network, for example, by conforming to Bluetooth standards. Other wireless network interfaces and/or protocols can also be supported.

IEEE 802.11b corresponds to IEEE Std. 802.11b-1999 entitled "Local and Metropolitan Area Networks, Part 11: Wireless LAN Medium Access Control (MAC) and Physical Layer (PHY) Specifications: Higher-Speed Physical Layer Extension in the 2.4 GHz Band," approved Sep. 16, 1999 as well as related documents. IEEE 802.11g corresponds to IEEE Std. 802.11g-2003 entitled "Local and Metropolitan Area Networks, Part 11: Wireless LAN Medium Access Control (MAC) and Physical Layer (PHY) Specifications, Amendment 4: Further Higher Rate Extension in the 2.4 GHz Band," approved Jun. 27, 2003 as well as related documents. Bluetooth protocols are described in "Specification of the Bluetooth System: Core, Version 1.1," published Feb. 22, 2001 by the Bluetooth Special Interest Group, Inc. Associated as well as previous or subsequent versions of the Bluetooth standard may also be supported.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

While the invention has been described in terms of several embodiments, those skilled in the art will recognize that the invention is not limited to the embodiments described, but can be practiced with modification and alteration within the spirit and scope of the appended claims. The description is thus to be regarded as illustrative instead of limiting.

What is claimed is:

1. An apparatus comprising:
a light source to provide unpolarized light;
a pellicle positioned to reflect the light toward a device under test (DUT),
an optical half wave plate positioned to receive the reflected light from the pellicle and to pass the reflected light to the DUT, and to pass light reflected by the DUT;
wherein the reflected light from the DUT passed by the optical half wave plate is directed to the pellicle and passes through the pellicle; and
a camera to receive the light passed through the pellicle for backside imaging;
wherein optical half wave plate is adjusted to impose a correct polarization orientation of light, through silicon, onto asymmetrical structure layout attributes of the DUT.

2. The apparatus of claim 1 further comprising an optical linear polarizer positioned to receive light from the light source and to provide polarized light.

3. The apparatus of claim 1 wherein the optical half wave plate is in a fixed position.

4. The apparatus of claim 1 wherein the optical half wave plate is rotatable.

5. The apparatus of claim 1 wherein the optical half wave plate is rotatable.

6. The apparatus of claim 1 further comprising a computing device coupled with the camera, the computing device to receive a first image captured by the camera when the optical half wave plate is in a first orientation and to receive a second image captured by the camera when the optical half wave plate is in a second orientation, wherein the computing device generates an output image corresponding to a difference between the first image and the second image.

7. A method comprising:
transmitting unpolarized light from a light source;
reflecting the light toward a device under test (DUT) with a pellicle;

passing the reflected light through an optical half wave plate positioned between the pellicle and the DUT;

passing light reflected from the DUT through the optical half wave plate to the pellicle;

passing the light from the optical half wave plate through the pellicle;

wherein optical half wave plate is adjusted to impose a correct polarization orientation of light, through silicon, onto asymmetrical structure layout attributes of the DUT.

8. The method of claim 7 further comprising polarizing the unpolarized light with an optical linear polarizer to generate polarized light.

9. The method of claim 7 further comprising capturing an image represented by the light passed through the pellicle with an image capture device.

10. The method of claim 9 further comprising:
receiving a first image captured by the image capture device when the optical half wave plate is in a first orientation,
receiving a second image captured by the image capture device when the optical half wave plate is in a second orientation
generating an output image corresponding to a difference between the first image and the second image.

11. The method of claim 7 wherein the optical half wave plate is not rotated.

12. The method of claim 7 wherein the optical half wave plate is rotated.

13. The method of claim 7 wherein the optical half wave plate is rotatable under control of a host test device.

14. An apparatus comprising:
a light source to provide unpolarized light;
a pellicle positioned to reflect the unpolarized light toward a device under test (DUT), the pellicle further to pass light reflected by the DUT;
an optical linear polarizer positioned to receive light passed through the pellicle and to provide polarized light;
wherein the reflected light from the DUT passed by the optical linear polarizer is directed to an image capture device and the optical half wave plate is adjusted to impose a correct polarization orientation of light, through silicon, onto asymmetrical structure layout attributes of the DUT.

15. The apparatus of claim 14 wherein the optical half wave plate is in a fixed position.

16. The apparatus of claim 14 wherein the optical half wave plate is rotatable.

17. The apparatus of claim 14 wherein the optical half wave plate is rotatable.

18. The apparatus of claim 14 further comprising a camera to receive the light passed through the pellicle.

* * * * *